(12) United States Patent
Hong et al.

(10) Patent No.: US 6,426,202 B1
(45) Date of Patent: Jul. 30, 2002

(54) **NYSTATIN-RESISTANT *ASPERGILLUS TERREUS* CLS 247-13, KCTC 0673BP FOR PREPARING TRIOL HEPTANOIC ACID EMPLOYING THE SAME**

(75) Inventors: Chung-II Hong, Chicago, IL (US); Kyung-Hwan Kim; Byoung-Taek Choi, both of Seoul (KR); Jang Woo Park, Kyunggi-do (KR); Nak Kyu Sung, Kyunggi-do (KR); Byoung Kook Kim, Kyunggi-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 09/869,440

(22) PCT Filed: Oct. 30, 2000

(86) PCT No.: PCT/KR00/01236

§ 371 (c)(1),
(2), (4) Date: Jun. 26, 2001

(87) PCT Pub. No.: WO01/30975

PCT Pub. Date: May 3, 2001

(30) Foreign Application Priority Data

Oct. 29, 1999 (KR) ............................................ 99-47379

(51) Int. Cl.[7] .............................. C12P 7/42; C12N 1/18; C12N 1/14
(52) U.S. Cl. ................. 435/146; 435/254.1; 435/254.3; 435/256.1; 435/913
(58) Field of Search ............................. 435/146, 254.3, 435/254.1, 256.1

(56) References Cited

U.S. PATENT DOCUMENTS

| | | | |
|---|---|---|---|
| 4,231,938 A | 11/1980 | Monaghan et al. | |
| 5,223,415 A | 6/1993 | Conder et al. | |
| 5,250,435 A | 10/1993 | Cover et al. | |
| 5,925,551 A | 7/1999 | Hong et al. | |

FOREIGN PATENT DOCUMENTS

| | | |
|---|---|---|
| EP | 0 517 413 A1 | 12/1992 |
| WO | WO 95/12661 | 5/1995 |

OTHER PUBLICATIONS

Snow, R., "An Enrichment Method for Auxotrophic Yeast Mutants Using the Antibiotic 'Nystatin,'" *Nature*, 211:206–207 (1966).

Endo, a., et al., "Monacolins J and L, New Inhibitors of Cholesterol Biosynthesis Produced by *Monasus ruber*," *J. Antibiotics* 38(3):420–422 (1985).

Moore, R., et al., "Biosynthesis of the Hypocholesterolemic Agent Mevinolin by *Aspergillus terreus*. Determination of the Origin of Carbon, Hydrogen, and Oxygen Atoms by $^{13}$C NMR andf Mass Spectrometry," *J. Am. Cham. Soc,* 107(12):3694–3701 (1985).

Shiao, M. et al., "Biosynthesis of Mevinolin, A Hypocholesterolemic Fungal Metabolite, in *Aspergillus terreus*," *Proc. Natl. Sci. Counc B. ROC.,* 11(3):223–231 (1987).

Mazumder, C., et al., "Changes in Membrane Lipids and Amino Acid Transport in a Nystatin–Resistant *Aspergillus niger*," *Can. J. Microbiol.* 36:435–437 (1990).

Kennedy, J., et al., "Modulation of Polyketide Synthase Activity by Accessory Proteins During Lovastatin Biosynthesis," *Science* 284:1368–1372 (1999).

*Primary Examiner*—David M. Naff
*Assistant Examiner*—Kailash C. Srivastava
(74) *Attorney, Agent, or Firm*—Knobbe, Martens, Olson & Bear, LLP

(57) ABSTRACT

A nystatin-resistant mutant microorganism belonging to *Aspegillus* genus is provided for preparing triol heptanoic acid, a precursor of 3-hydroxy-3-methylglutaryl-CoA reductase inhibitor. A mutant *Aspergillus terreus* CLS247-13, KCTC 0673 BP is prepared by treating *Aspergillus terreus* CLS216-7, KCTC 0359 BP with ultraviolet ray or chemical mutagens. The mutant provides high productivity (at least 11.5 g/L, 95/6% of the total product) of triol heptanoic acid, while reducing (less than 0.53 g/L, 4.4% of total product) productivity of triol heptanoic acid analogues. Since the nystatin-resistant mutant strain CLS347-13 has a capability of producing triol heptanioc acid with a high yield in a short period of culture time compared with known triol heptanoic acid producing strains, it can be widely used in industrial applications.

7 Claims, 3 Drawing Sheets

NYSTATIN-RESISTANT *ASPERGILLUS TERREUS* CLS 247-13, KCTC 0673BP FOR PREPARING TRIOL HEPTANOIC ACID EMPLOYING THE SAME

This is the U.S. National Phase under 35 U.S.C. §371 of International Application PCT/KR00/01236, filed Oct. 30, 2000, which clams priority of Korean Application No. 1999/47379, filed Oct. 29, 1999.

BACKGROUND OF THE INVENTION

1. Field of the Invention

The present invention relates to a novel nystatin-resistant microorganism belonging to Aspergillus genus and a process for preparing triol heptanoic acid, a precursor of 3-hydroxy-3-methylglutaryl-coenzyme A ("HMG-CoA") reductase inhibitor by employing the said microorganism, more specifically, to a novel nystatin-resistant mutant which provides a high productivity of triol heptanoic acid with minimal productivity of analogues therefrom, produced by introducing mutations into a protoplast fusion mutant strain *Aspergillus terreus* CLS216-7 producing mevinolinic acid with a high yield and a process for preparing triol hedtanoic acid by aerobic submerged culture of the novel mutant strain in a nutrient medium.

2. Description of the Prior Art

Hyperlipidemia is known as one of the major factors for development of cardiovascular disease, the leading cause of death. The substances developed for treatment of hyperlipidemia are mostly inhibitors of HMG-CoA reductase involved in the cholesterol biosynthesis, and are useful for treatment of hypercholesterolemia and hyperlipidemia in human body.

Lovastatin, developed first and now commercially available as a therapeutic agent against hyperlipidemia, is produced by fermentation of fungi and specific microorganisms, for example, *Aspergillus terreus* (see: Korean patent publication No. 83-2438; U.S. Pat. No. 4,231,936) or Monascus genus (see: Korean patent publication No. 83-2329). Lovastatin is also a starting material for the synthesis of simvastatin, a potent inhibitor of HMG-CoA reductase (see: U.S. Pat. No. 5,223,415).

Triol heptanoic acid, chemically represented as 7-[1,2,6,7,8,8a(R)-hexahydro-2(S), 6(R)-dimethyl-8(S)-hydroxy-1(S)-naphthyl]-3(R),5(R)-dihyroxyheptanoic acid, serves as a starting material for the synthesis of simvastatin or other 8-ester analogues which function as potent HMG-CoA reductase inhibitors (see: Korean patent publication No. 85-669). Triol heptanoic acid can be produced by chemical hydrolysis of lovastatin, fermentation of *Monascus ruber* (see: Japanese patent laid-open publication No. 86-13798; Endo et al., *The Journal of Antibiotics*, 38(3):420–422, 1985), or fermentation of mutated *Aspergillus terreus* MF-4833, a mevinolinic acid-producing microorganism (see: U.S. Pat. No. 5,250,435).

Mevinolinic acid, produced by *Aspergillus terreus*, is biosynthesis via polyketide pathway in a similar manner to the fatty acid and sterol biosynthesis (see: Moore et al., *J. Am. Chem. Soc.*, 107:3694–3701, 1985), and it has 2 methyl groups transferred from S-adenosyl methionine (SAM) (see: Shiao, M. S. and Pon, H. S., *Proc. Nat. Sci. Counc. B. Roc.*, 11:223–231, 1987). Recently, two polyketide-synthesizing enzymes engaged in forming a backbone consisting of 9 acetate units and genes thereof were isolated from *Aspergillus terreus*. Analysis of the genes encoding an enzyme synthesizing 2-methylbutyrate side chain of mevinolinic acid and an enzyme adding the side chain to triol heptanoic acid, backbone of mevinolinic acid, revealed that their deduced amino acid sequences and presumed active sites are almost similar to those of a fatty acid synthetase (see: WO95/12661; Kennedy, J. et al., *Science*, 284:1368–1372, 1999).

In mutant strains of *Aspergillus terreus* and yeasts resistant to nystatin, a kind of polyenic macrolide antibiotics, which affects biosynthesis of fatty acids and sterols and cell membrane permeability, the nystatin makes some changes in fatty acid and sterol compositions of cell membrane (see: Mazumder, C. et al., *Lipids,* 22(9):609–612, 1987) and also affects the biosynthesis of secondary metabolites in the mutants (see: Liu, Y. T., *Proc. Natl. Sci. Counc. Repub. China* [B], 8(2):182–186, 1984).

Meanwhile, by mutating a disclosed strain of mevinolinic acid-producing *Aspergillus terreus* using nitrosoguanidine, it has been reported that the triol heptanoic acid was produced up to 5.95 g/L and the product on of mevinolinic acid was markedly reduced in a 14 day-fermentation process (see: European patent publication No. 0517413A1).

However, it has revealed a shortcoming that the fermentation process is time consuming and produces analogues of triol heptanoic acid with a high level, which naturally limits the application of fermentation process for producing simvastatin or 8-ester analogues, in industrial scale. In this regard, the chemical hydrolysis of lovastatin has prevailed in the art, since it is rather advantageous for the production of triol heptanoic acid. The production of triol heptanoic acid from lovastatin by chemical hydrolysis is, however, proven to be less satisfactory in a sense that the cost is very high.

Accordingly, there are strong reasons for exploring and developing a novel microbe which produces triol heptanoic acid with a high yield and has relatively short fermentation time to reduce cost and production period.

SUMMARY OF THE INVENTION

The present inventors isolated a novel mutant strain *Aspergillus terreus* CLS247-13 resistant to nystatin, an inhibitor of fatty acid and sterol biosynthesis, by treating *Aspergillus terreus* strain producing mevinolinic acid with conventional mutagens known in the art, followed by selecting a mutant strain producing triol heptanoic acid with a high yield while producing only a little triol heptanoic acid analogues during a short period of fermentation and maintaining its genetic characteristics stably through many generations.

A primary object of present invention is,, therefore, to provide a novel microorganism belonging to Aspergillus genus, which shows resistance to nystatin and produces triol heptanoic acid with a high yield.

The other object of the invention is to provide a process for preparing triol heptanoic acid employing the said microorganism.

BRIEF DESCRIPTION OF THE DRAWINGS

The above, the other objects and features of the invention will become apparent from the following descriptions given in conjunction with the accompanying drawings, in which.

DETAILED DESCRIPTION OF THE INVENTION

Figure 2:
FIG. 2 is an HPLC chromatogram of acetone extract of culture broth of a nystatin-resistant mutant strain, *Aspergillus terreus* CLS247-13.

The present invention provides a nystatin-resistant mutant strain *Aspergillus terreus* capable of producing at least 11.5 g/L of triol heptanoic acid. The present invention also provides a process for preparing triol heptanoic acid by aerobic submerged culture of the said microorgnism in a nutrient medium. The mutant strain of the invention, obtained by treating *Aspergillus terreus* CLS216-7 (KCTC 0359BP) with ultraviolet ray or chemical mutagens, provides a high productivity of triol heptanoic acid (at least 11.5 g/L, 95.6% of total product) while showing reduced productivity of triol heptanoic acid analogues (less than 0.53 g/L, 4.4% of total product)

The present invention is further illustrated as follows.

Inspired by the previous reports for: biosynthetic pathway of, mevinolinic acid occurring via polyketide pathway similar to the pathway of fatty acid and sterol biosynthesis; the disclosed information about mevinolinic acid synthetase and its gene (see: WO95/12661; Kennedy, J. et al., *Science*, 284:1368–1372, 1999); and, furthermore, the fact that triol heptanoic acid can be converted into mevinolinic acid by *Paecilomyces viridis* and cell extract of *Monascus ruber* known to produce various mevinolinic acid analogues including mevinolinic acid (see: Kimura, K. et al., *The Journal of Antibiotics*, 43(12): 1621–1622,, 1990), the present inventors have found that it can be blocked for *Aspergillus terreus* producing mevinolinic acid with a high yield to synthesize a side chain consisting of 2 acetate units or to transfer the side chain to a backbone consisting of 9 acetate units in mevinolinic acid structure by introducing mutations into *Aspergillus terreus*. Furthermore, the present inventors have found that the mutant strain with a high productivity of triol heptanoic acid can be developed by inducing changes in fatty acid and sterol biosynthesis pathway to give maximum supply of precursors and reduced side reactions, based on the fact that fungi resistant to polyenic macrolide antibiotics including nystatin showed changes in biosynthetic pathway and composition of fatty acids and sterols, which is similar to polyketide antibiotics pathway, as well as the fact that the acetate precursors used for biosynthesis of fatty acids and sterols are common to those used for biosynthesis of polyketide antibiotics.

The *Aspergillus terreus* CLS216-7 (KCTC 0359BP, hereinafter, referred to as 'parent strain CLS216-7') producing mevinolinic acid with a high yield (see: U.S. Pat. No. 5,925,551) was employed as a parent strain to obtain a mutant strain resistant to nystatin. To obtain a nystatin-resistant mutant, the parent strain CLS216-7 was cultured in agar slant medium to harvest spores. Then, the spore suspension was treated with conventional mutagens, such as ultraviolet ray or chemical mutagens. After removal of rapid-growing parent and mutant strains by the method of Richard Snow (see: Snow, R., *Nature*, 211:206–207, 1966) which was employed to increase selection efficiency of mutants, the nystatin-resistant mutants were screened using a medium containing nystatin. Colonies formed on a nystatin-containing medium were selected and cultured in a liquid medium. Many colonies producing various kinds of mevinolinic acid analogues had appeared. Among them, a mutant producing triol heptanoic acid as the predominant product (at least 11.5 g/L) while producing a minimum amount of triol heptanoic acid analogues (less than 0.53 g/L) with almost no production of mevinolinic acid (less than 0.03 mg/L) was selected and named '*Aspergillus terreus* CLS247-13' (hereinafter, referred to as 'mutant strain CLS247-13'), which was deposited with an international depository authority, the Korean Collection for Type Cultures (KCTC, #52, Oun-dong, Yusong-ku, Taejon, Republic of Korea) affiliated to Korea Research institute of Bioscience and Biotechnology (KRIBB), under Accession (deposition) No. KCTC 0672BP.

The most prominent characteristics of the nystatin-resistant strain thus obtained has proved to be a high productivity of triol heptanoic acid with a low productivity or triol heptanoic acid analogues compared with the parent strain. It has been proved that the mutant strain CLS247-13 has a capability of producing triol heptanoic acid with higher amount for a shorter culture period compared with a known triol heptanoic acid-producing strain by showing that it is able to accumulate at least 11.5 g/L for a 12-day culture period. Also, the mutant strain CLS247-13 showed 8-fold increase in resistance to nystatin, 29% decrease in oleic acid content and 25% increase in ergosterol content of cell membrane composition, and 3-fold increase in spore formation ability on a solid medium compared with the parent strain CLS216-7.

The mutant strain CLS247-13 with a high yield of triol heptanoic acid selected in the present invention may be cultured in a medium comprising carbon source, nitrogen source, inorganic substances, anti-foaming agent, etc., at a temperature range of 25–36° C., Preferably 27–30° C. under a pH condition of 5.5–7.5. In this connection, lactose, dextrin, maltose, starch, soluble starch, fructose, sucrose, xylose, glucose, galactose and glycerol may be used as a carbon source alone or in combination. For example, combination of lactose and dextrin, lactose and soluble starch, lactose and starch, or maltose and soluble starch may be used as a carbon source. Organic and inorganic nitrogen source such as corn steep liquor, dried yeast, peptone, casein, soy bean flour, ammonium sulfate, ammonium nitrate and sodium nitrate may be used as a nitrogen source alone or in combination. Although inorganic substances may be varied depending on medium used, iron, manganese, copper, calcium, boron, molybdenum and zinc are preferably employed as inorganic substances. Commercially available PPG 2,000 (polypropylene glycol 2,000) and the like may be used as anti-foaming agents.

Production of triol heptanoic acid from the mutant strain CLS247-13 may be performed according to the known method for obtaining secondary metabolites by culturing a strain of Aspergillus genus. Since triol heptanoic acid is accumulated in an acid form in culture medium and mycelium, it can be recovered in a form of triol lactone through extraction step after mixing them with organic solvents such as acetone in accordance with a known method in the art.

The present invention is further illustrated in the following examples, which should not be taken to limit the scope of the invention.

EXAMPLE 1

Preparation of *Aspergillus terreus* CLS247-13

*Aspergillus terreus* CLS247-13 resistant to nystatin of the invention was prepared by using a parent strain, i.e., the mutant strain *Aspergillus terreus* CLS216-7 (KCTC 03598BP) having a high productivity of mevinolinic acid and a low productivity of its analogies.

EXAMPLE 1-1
Concentration of Mutant Strains

In order to obtain spores of *Aspergillus terreus* CLS216-7 having a high productivity of mevinolinic acid, the spore suspension stored in −70° C. freezer or the colony selected from a solid culture was spreaded onto the solid complex medium disclosed in Table 1. The spreaded solid complex medium was incubated at 28° C. for 20 days, and the spores were recovered in 5 ml of 20% glycerin solution to give spore suspensions. The spore suspensions thus obtained were washed with saline solution, irradiated with ultraviolet ray in a strength of 300 $\mu W/cm^2$ for 2 minutes, and then the efficiency of mutant selection was increased by the method of Richard Snow (see: Snow, R., *Nature*, 211:206–207, 1966): The spore suspensions were inoculated, in a ratio of 5% (v/v) against the medium, into 30 ml aliquots of liquid minimal medium whose composition is the same as that of solid minimal medium disclosed in Table 1 except for omitting agar and adding 1% yeast extract in a 100 ml-triangular flask, and the resultant culture was incubated at 28° C. on a shaking incubator at 230 rpm under a dark condition for 24–30 hours. And then, the culture was washed with saline solution, and the spores ($1.0 \times 10^7$ spores per ml of medium) were inoculated into 30 ml aliquots of liquid minimal medium omitting ammonium sulfate (nitrogen starved-medium) in a 100 ml-triangular flask and incubated under the condition described above for 5–10 hours.

TABLE 1

The composition of solid complex medium and minimal solid medium

| Solid Complex Medium | | Minimal Solid Medium | |
|---|---|---|---|
| Component | Composition Ratio | Component | Composition Ratio |
| Glucose | 4 g/L | Glucose | 50 g/L |
| Malt extract | 10 g/L | Ammonium Sulfate | 3 g/L |
| Yeast extract | 4 g/L | Potassium phosphate | 1 g/L |
| Agar | 20 g/L | Magnesium sulfate | 1 g/L |
| | | Trace element mixture* | 1 ml/L |
| | | Agar | 20 g/L |

*indicates a mixture of $FeSO_4 \cdot 7H_2O$ 1.0 g/L, $MnSO_4 \cdot H_2O$ 0.5 g/L, $CuSO_4 \cdot 2H_2O$ 0.025 g/L, $CaCO_3$ 0.15 g/L, $H_3BO_3$ 0.056 g/L, $(NH_4)_6Mo \cdot 4H_2O$ 0.010 g/L, $ZnSO_4 \cdot 7H_2O$ 0.2 g/L and 0.5 N HCl 10 ml/L.

The nitrogen-starved culture was washed with saline solution 2 times, and centrifuged, suspended and concentrated. And then, it was inoculated, in a ratio of 10% (v/v) against the medium, into 20 ml aliquots of liquid minimal medium containing ammonium sulfate in a 100 ml-triangular flask, and the resultant was incubated at 28° C. on a shaking incubator at 230 rpm for 3–5 hours before 80 $\mu g/ml$ of nystatin was added, and the incubation was continued for 1.5–3 hours.

EXAMPLE 1-2
Preparation of *Aspergillus terreus* CLS247-3

After incubating the culture in a liquid minimal medium containing nystatin for 1.5–3 hours, it was washed with saline solution, concentrated, diluted properly, and spreaded onto solid minimal medium containing 150 $\mu g/ml$ of nystatin, and then the resultant was incubated at 28° C. for 8–15 days to isolate viable mutant strains. The isolated mutant strains resistant to nystatin, showing various morphological characteristics, were subcultured on solid minimal media containing increasing concentrations of nystatin (i.e., 150, 160, 170, 180, 190 and 200 mg of nystatin per ml) to select mutants showing increased resistance. The nystatin-resistant mutants thus obtained were incubated in an agar slant medium for 15–20 days. The spores formed were recovered in a 20% glycerin solution and subjected to liquid culture as disclosed in Example 2 below. As a result, the productivity of mevinolinic acid decreased and a variety of its analogues appeared. The mutant showing a high productivity of triol heptanoic acid of at least 11.5 g/L was selected and named '*Aspergillus terreus* CLS247-13'. *Aspergillus terreus* CLS247-13 maintained morphological characteristics, resistance to nystatin and high productivity of triol heptanoic acid constantly on a solid minimal medium containing 2 g/L of yeast extract for 10 generations. The mutant strain of the invention, *Aspergillus terreus* CLS247-13 was deposited with an international depository authority, the Korean Collection for Type Cultures (KCTC, #52, Oun-dong, Yusong-ku, Taejon, Republic of Korea) affiliated to Korea Research Institute of Bioscience and Biotechnology (KRIBB), under Accession (deposition) No. KCTC 0672BP on Oct. 20, 1999.

EXAMPLE 2
Liquid Culture of *Aspergillus terreus* CLS247-13 and the Analysis of Culture Broth For liquid culture, a seed culture was grown by inoculating the suspension of spores, in a ratio of 5% (v/v) against the medium, into 30 ml of seed culture medium as disclosed in Table 2 in a 100 ml-triangular flask, followed by incubating at 28° C. on a shaking incubator at 230 rpm for 24–48 hours depending on growth state of the strain. The seed culture broth was inoculated, in a ratio of 10% (v/v) against the main culture medium, into 30 ml of main culture medium as disclosed in Table 2 in a 100 ml-triangular flask, and then incubated at 28° C. on a shaking incubator at 230 rpm for 10–15 days depending on growth state of the strain.

The 3 ml of main culture broth was mixed with 3 ml of acetone, stirred at 28° C. on a shaking incubator at 230 rpm for 30 minutes, and centrifuged. The aliquot of supernatant was subject to HPLC analysis under the condition described below.

TABLE 2

The composition of seed culture medium and main culture medium

| Seed Culture Medium | | Main Culture Medium | |
|---|---|---|---|
| Component | Composition Ratio | Component | Composition Ratio |
| Soluble starch | 10 g/L | Soluble starch | 200 g/L |
| Glucose | 10 g/L | Soybean flour | 40 g/L |
| Corn steep liquor | 4 g/L | Yeast extract | 1 g/L |
| Soybean flour | 10 g/L | Phosphate | 0.05 g/L |
| Soybean oil | 2.5 g/L | PPG2000 | 5 ml/L |
| Trace element mixture* | 10 ml/L | Trace element mixture* | 5 ml/L |

*indicates a mixture of $FeSO_4 \cdot 7H_2O$ 1.0 g/L, $MnSO_4 \cdot H_2O$ 0.5 g/L, $CuSO_4 \cdot 2H_2O$ 0.025 g/L, $CaCO_3$ 0.15 g/L, $H_3BO_3$ 0.056 g/L, $(NH_4)_6Mo_7 \cdot 4H_2O$ 0.010 g/L, $ZnSO_4 \cdot 7H_2O$ 0.2 g/L and 0.5 N HCl 10 ml/L.

Condition on for HPLC analysis:

Column: Partisil 50DS-3(3 $\mu m$, 4.6×250 cm, Whatman, USA)

Mobile phase: acetonitrile: 0.1% $H_3PO_4$ in D.W.=60:40 (v/v)

Temperature: room temperature

Flow rate of mobile phase: 1.0 ml/min

Detection: 235 nm

EXAMPLE 3

Mycological Characteristics of the Mutant Strain CLS247-13 and the Parent Strain CLS216-7

Figure 1:
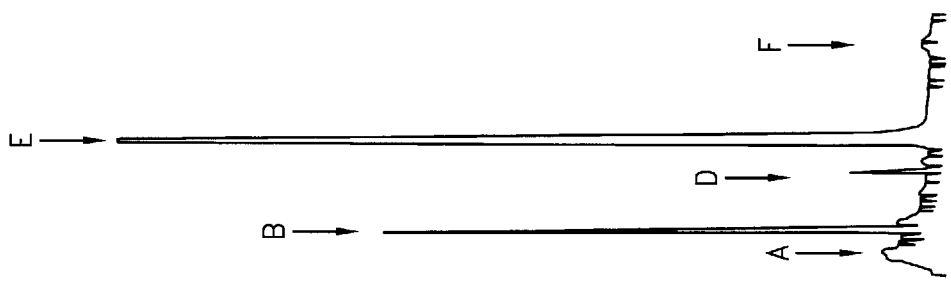
FIG. 1 is an HPLC chromatogram of acetone extract 0f culture broth of parent strain, *Aspergillus terreus* CLS216-7.

The characteristics of the parent strain CLS216-7 producing mevinolinic acid with a high yield and those of the mutant strain CLS247-13 resistant to nystatin were compared and summarized in Table 3. The remarkable characteristics of the nystatin-resistant mutant strain CLS247-13 which are different from the parent strain CLS216-7 producing mevinolinic acid with a high yield are its ability to accumulate triol heptanoic acid at high concentration (at least 11.5 g/L), while accumulating only a little triol heptanoic acid analogues in a culture broth. Thus, the content of triol heptanoic acid reached at least 95.6% of total products (see: FIGS. 1 and 2).

Figure 3:
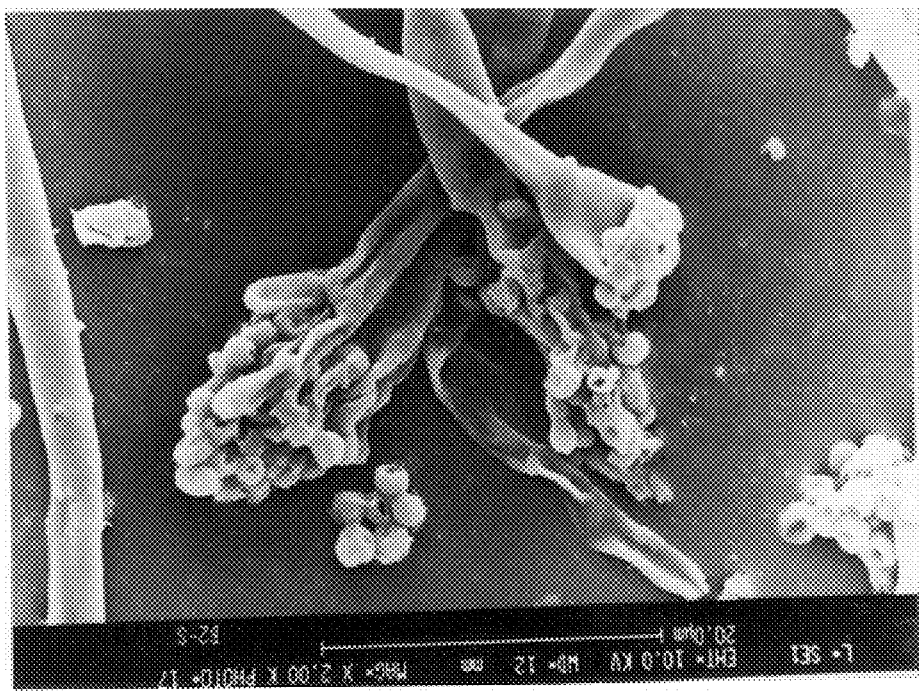
FIG. 3 is an electron micrograph of spores of parent strain *Aspergillus terreus* CLS216-7.
Figure 4:
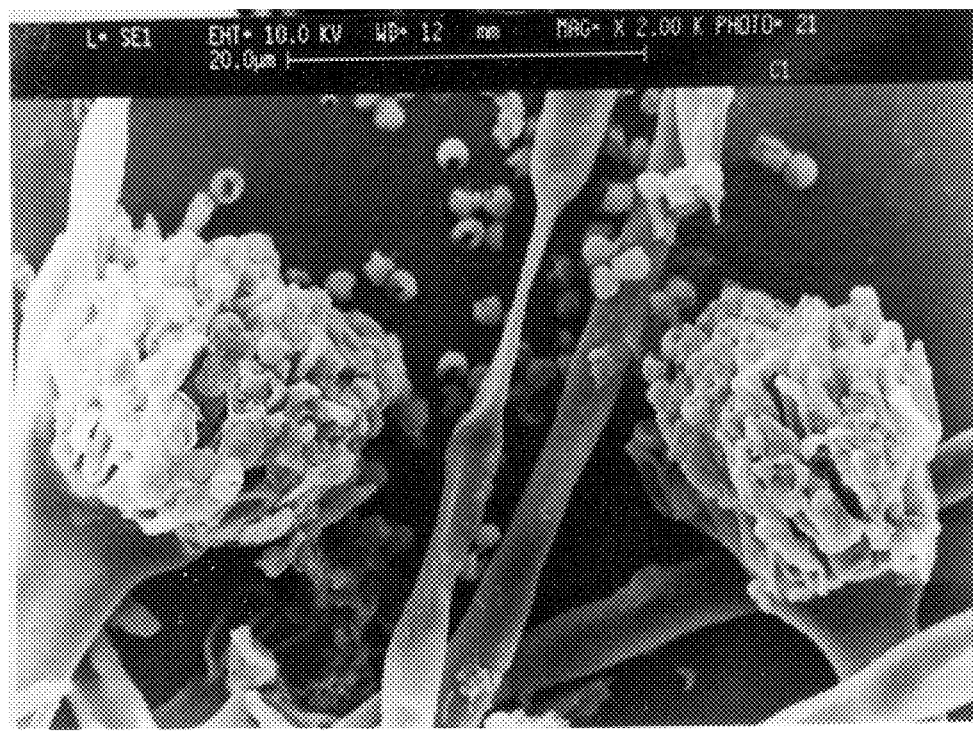
FIG. 4 is an electron micrograph of spores of mutant strain of the invention, *Aspergillus terreus* CLS247-13 resistant to nystatin.

Although the growth rate of the nystatin-resistant mutant strain CLS247-13 was somewhat lower than that of the parent strain CLS216-7 in both solid and liquid cultures, the sporulation ability of the mutant strain CLS247-13 was found to be 3 times higher than that of the parent strain CLS216-7 on a solid medium. The morphological characteristics of both strains were examined under an electron microscope after culturing on a solid complex medium for 15 days and the electron micrographs of them are compared (see: FIGS. 3 and 4). As shown in FIGS. 3 and 4, the nystatin-resistant mutant strain CLS247-13 of the invention has morphological characteristics of thicker stalks, bigger conidiophores and larger number of spores per conidiophore (3 times more in C.F.U. than parent) compared with he parent strain CLS216-7.

Since the mutant strain of the invention, resistant to nystatin which is known to affect the biosynthesis of fatty acids and sterols and their composition in cell membrane, showed remarkable differences in cell growth from the parent strain, the contents of fatty acids and sterols were analyzed according to the method of Hosobuchi (see: Hosobuchi, et al., *Biosci. Biochem.*, 57:1414–1419, 1993). As shown in Table 3 below, contents of oleic acid decreased 29% but contents o ergosterol increased 25% in cell membrane composition of the mutant strain CLS247-13, and the minimal inhibitory concentration of nystatin increased 8-fold, when compared with those of the parent strain CLS216-7.

TABLE 3

Characteristics of parent strain CLS216-7 and mutant strain CLS247-13

| Characteristics | Parent strain CLS216-7 | Mutant strain CLS247-13 |
|---|---|---|
| Sporulation | $1.1 \times 10^7$/ml C.F.U. | $3.5 \times 10^7$/ml C.F.U. |
| Minimal inhibitory conc. of nystatin | $\leq 25$ μg/ml | $\leq 200$ μg/ml |
| Oleic acid conc. (μg/ml dry cell) | 2.4 | 1.7 |
| Ergosterol conc. (μg/ml dry cell) | 0.40 | 0.50 |
| [a]Productivity of triol heptanoic acid | [c]ND | 11.5 g/L |
| [b]Content of triol heptanoic acid | [c]ND | 95.6% |

[a]Fermented for 12 days in main culture broth in Table 2
[b]Content of triol heptanoic acid among triol heptanoic acid and derivatives thereof on chromatogram according to HPLC analysis condition in Example 2
[c]ND: not detected FIGS. 1 and 2 are HPLC chromatograms of acetone extract of culture broth of the parent strain *Aspergillus terreus* CLS216-7 and the nystatin-resistant mutant strain CLS247-13, respectively. In FIGS. 1 and 2, A, B, C, D, E and F represent organic acid, acetone, triol heptanoic acid, triol heptanic acid analogues, mevinolinic acid and mevinolin, respectively.

As clearly illustrated and demonstrated above, the present invention provides a nystatin-resistant microorganism belonging to Aspergillus genus and a process for preparing triol heptanoic acid, a precursor of 3-hydroxy-3-methylglutaryl-CoA reductase inhibitor employing the same. The mutant strain of *Aspergillus terreus* CLS247-13 (KCTC 0672BP), prepared by treating *Aspergillus terreus* CLS216-7 (KCTC 0359BP) with ultraviolet ray or chemical mutagens, provides a high productivity of triol heptanoic acid (at least 11.5 g/L, 95.6% of total product) while reducing productivity of triol heptanoic acid analogues (less than 0.53 g/L, 4.4% of total product). Since the nystatin-resistant mutant strain CLS247-13 has a capability of producing triol heptanoic acid with a high yield for a short period of culture time compared with known triol heptanoic acid-producing strains, it can be widely used in industrial applications.

Various modifications of the invention in addition to those shown and described herein will be apparent to those skilled in the art from the foregoing descriptions. Such modifications are also intended to fall within the scope of the appended claims.

What is claimed is:

1. A nystatin-resistant *Aspergillus terreus* CLS247-13, KCTC 0672BP which is capable of producing at least 11.5 g/L of triol heptanoic acid under culture conditions, while producing less than 0.53 g/L triol heptanoic acid analogues.

2. A process for preparing triol heptanoic acid by aerobic culture of the *Aspergillus terreus* CLS247-13 KCTC 0672BP of claim 1 in a nutrient medium and obtaining triol heptanoic acid therefrom.

3. The process for preparing triol heptanoic acid of claim 2, wherein *Aspergillus terreus* CLS247-13 KCTC 0672BP is cultured in a medium comprising carbon source, nitrogen source, anti-foaming agent, and inorganic substances at a temperature range of 25–36° C. under a pH condition of 5.5–7.5.

4. The process for preparing triol heptanoic acid of claim 3, wherein the carbon source is selected from the group consisting of lactose, dextrin, maltose, starch, soluble starch, fructose, sucrose, xylose, glucose, galactose and glycerol.

5. The process for preparing triol heptanoic acid of claim 3, wherein the nitrogen source is selected from the group consisting of corn steep liquor, dried yeast, peptone casein, soy bean flour, ammonium sulfate, ammonium nitrate and sodium nitrate.

6. The process for preparing triol heptanoic acid of claim 3, wherein the inorganic substance is selected from the group consisting of iron, manganese, copper, calcium, boron, molybdenum and zinc.

7. The process for preparing triol heptanoic acid of claim 3, wherein the anti-foaming agent is polypropylene glycol 2,000.

* * * * *